United States Patent
Sajja et al.

(10) Patent No.: US 8,063,214 B2
(45) Date of Patent: Nov. 22, 2011

(54) POLYMORPHIC FORMS OF TADALAFIL

(75) Inventors: Eswaraiah Sajja, Hyderabad (IN);
Venkata Naga Kali Vara Prasada Raju Vetukuri, Hyderabad (IN); Srinivas Reddy Ningam, Medak (IN); Ravindra Vedantham, Hyderabad (IN); Rajyalakshmi Bodepudi, Guntur (IN)

(73) Assignees: Dr. Reddy's Laboratories Limited, Hyderabad, Andhra Pradesh (IN); Dr. Reddy's Laboratories, Inc., Bridgewater, NJ (US)

( * ) Notice: Subject to any disclaimer, the term of this patent is extended or adjusted under 35 U.S.C. 154(b) by 1001 days.

(21) Appl. No.: 11/577,948

(22) PCT Filed: Oct. 26, 2005

(86) PCT No.: PCT/US2005/038540
§ 371 (c)(1),
(2), (4) Date: Apr. 25, 2007

(87) PCT Pub. No.: WO2006/049986
PCT Pub. Date: May 11, 2006

(65) Prior Publication Data
US 2009/0131667 A1    May 21, 2009

Related U.S. Application Data

(60) Provisional application No. 60/622,887, filed on Oct. 28, 2004.

(51) Int. Cl.
*C07D 471/00* (2006.01)
*C07D 493/00* (2006.01)
(52) U.S. Cl. ...................... 544/343; 549/464
(58) Field of Classification Search .................. 544/343; 549/464
See application file for complete search history.

(56) References Cited

U.S. PATENT DOCUMENTS

| | | |
|---|---|---|
| 5,859,006 A | 1/1999 | Daugan |
| 5,981,527 A | 11/1999 | Daugan |
| 6,025,494 A | 2/2000 | Daugan |
| 6,127,542 A | 10/2000 | Daugan |
| 6,821,975 B1 | 11/2004 | Anderson |
| 2004/0147542 A1 | 7/2004 | Sawyer |
| 2004/0171830 A1 | 9/2004 | Orme |

FOREIGN PATENT DOCUMENTS

| | | | |
|---|---|---|---|
| EP | 1 336 602 A1 | | 8/2003 |
| WO | WO03/000691 A1 | | 1/2003 |
| WO | WO2004/011463 A1 | | 2/2004 |
| WO | WO 2005/116030 | * | 5/2005 |

OTHER PUBLICATIONS

Jiang, et al. Bioorganic & Medicinal Chemistry, 12, 2004, 1505-1515.*
Daugan, et al. Journal of Medicinal Chemistry, 46(21), 2003, 4533-4542.*
Gepner, et al., "Use of T.V. Modules in Chemistry," Chemistry in the Two-Year College, vol. XIV, 1975.

* cited by examiner

*Primary Examiner* — James O Wilson
*Assistant Examiner* — Douglas M Willis
(74) *Attorney, Agent, or Firm* — Thomas C. McKenzie; Balaram Gupta; Robert A. Franks (57) ABSTRACT

A process for preparing crystalline Form A of tadalafil (I), comprising crystallization from a solution of tadalafil in a solvent comprising a $C_3$-$C_7$ ester, a ketone, dimethylformamide, dimethylsulfoxide, ethanol, acetonitrile, a chlorinated hydrocarbon, t-butanol, N,N-dimethylacetamide, dioxane, N-methyl pyrrolidone, or a mixture of any two or more thereof.

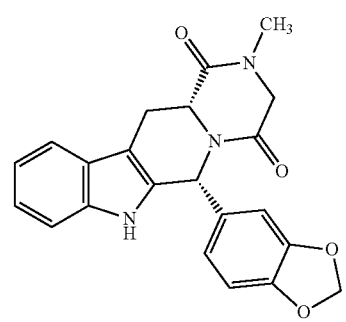

9 Claims, 6 Drawing Sheets

POLYMORPHIC FORMS OF TADALAFIL

INTRODUCTION TO THE INVENTION

The present invention relates to crystalline and amorphous forms of tadalafil and processes for their preparation.

Tadalafil has the chemical names: (6R,12aR)-2,3,6,7,12,12a-hexahydro-2-methyl-6-(3,4-methylenedioxyphenyl)-pyrazino[2,1:6,1]pyrido[3,4-b]indole-, 1,4-dione; and pyrazino[1',2':1,6]pyrido[3,4-b]indole-1,4-dione, 6-(1,3-benzodioxol-5-yl)-2,3,6,7,12,12a-hexahydro-2-methyl-, (6R,12aR)-; and can be depicted by the structure of Formula I.

TADALAFIL

Tadalafil is a potent and selective inhibitor of cyclic guanosine monophosphate (cGMP)-specific phosphodiesterase type 5 (PDE5), and is sold in pharmaceutical products using the trademark CIALIS™. Tadalafil is used in therapy for the treatment of a variety of conditions where inhibition of PDE5 is thought to be beneficial, such as the treatment of erectile disfunction.

U.S. Pat. No. 5,859,006 describes the compound tadalafil, related compounds, and methods for their synthesis.

U.S. Pat. No. 6,821,975 describes tadalafil in particulate form, wherein at least 90% of the particles have a particle size of less than about 40 microns, 25 microns, 15 microns or 10 microns, and pharmaceutical formulations using the particles.

Regulatory authorities require that efforts be made to identify all polymorphic forms, e.g., crystalline, amorphous, solvated, etc., of new drug substances, since polymorphic forms can vary in their chemical and physical properties. This variation frequently results in bioavailability, stability, and other differences between production lots of formulated pharmaceutical products.

However, the existence, and possible numbers, of polymorphic forms for a given compound cannot be predicted. In addition, there are no "standard" procedures that can be used to prepare polymorphic forms of a substance.

Accordingly, there remains a need to prepare additional polymorphic forms of tadalafil.

SUMMARY OF THE INVENTION

The present invention provides amorphous and crystalline form B of tadalafil, and mixtures of Forms A and B of tadalafil.

In one aspect, the present invention provides a process for the preparation of amorphous and crystalline Form B of tadalafil, and mixtures of Form A and Form B of tadalafil.

The present invention provides processes for preparing substantially pure crystalline tadalafil Form A by crystallization, crystallization from solvent/antisolvent, removal of solvent, or by drying a solvate of tadalafil.

In another aspect, the present invention provides a process for preparing substantially pure crystalline tadalafil Form B by dissolving tadalafil in a ketonic solvent to form a solution, cooling the solution, maintaining the solution to obtain a precipitate, and recovering the precipitate.

In another aspect, the present invention provides a process for preparing a mixture of crystalline Form A and Form B of tadalafil by dissolving tadalafil in ester solvents to form a solution, distilling a part of solvent from the solution, cooling the solution, maintaining the solution to obtain a precipitate, and recovering the precipitate.

In yet another aspect, the present invention provides a process for preparing an amorphous form of tadalafil by dissolving tadalafil in an organic solvent to form a solution, and distilling the solvent from the solution to afford an amorphous form of tadalafil.

DETAILED DESCRIPTION

An aspect of the present invention provides crystalline Form B of tadalafil, mixtures of Form A and Form B of tadalafil, and amorphous tadalafil.

In an aspect, the present invention provides processes for the preparation of crystalline form A of tadalafil.

The various forms of tadalafil are characterized by their XRPD patterns, which differ between polymorpic forms. All XRPD results reported herein were obtained using Cu Kα radiation, having the wavelength 1.541 Å. The XRPD patterns of the figures have a vertical axis that is intensity units, and a horizontal axis that is degrees 2θ.

Figure 1:
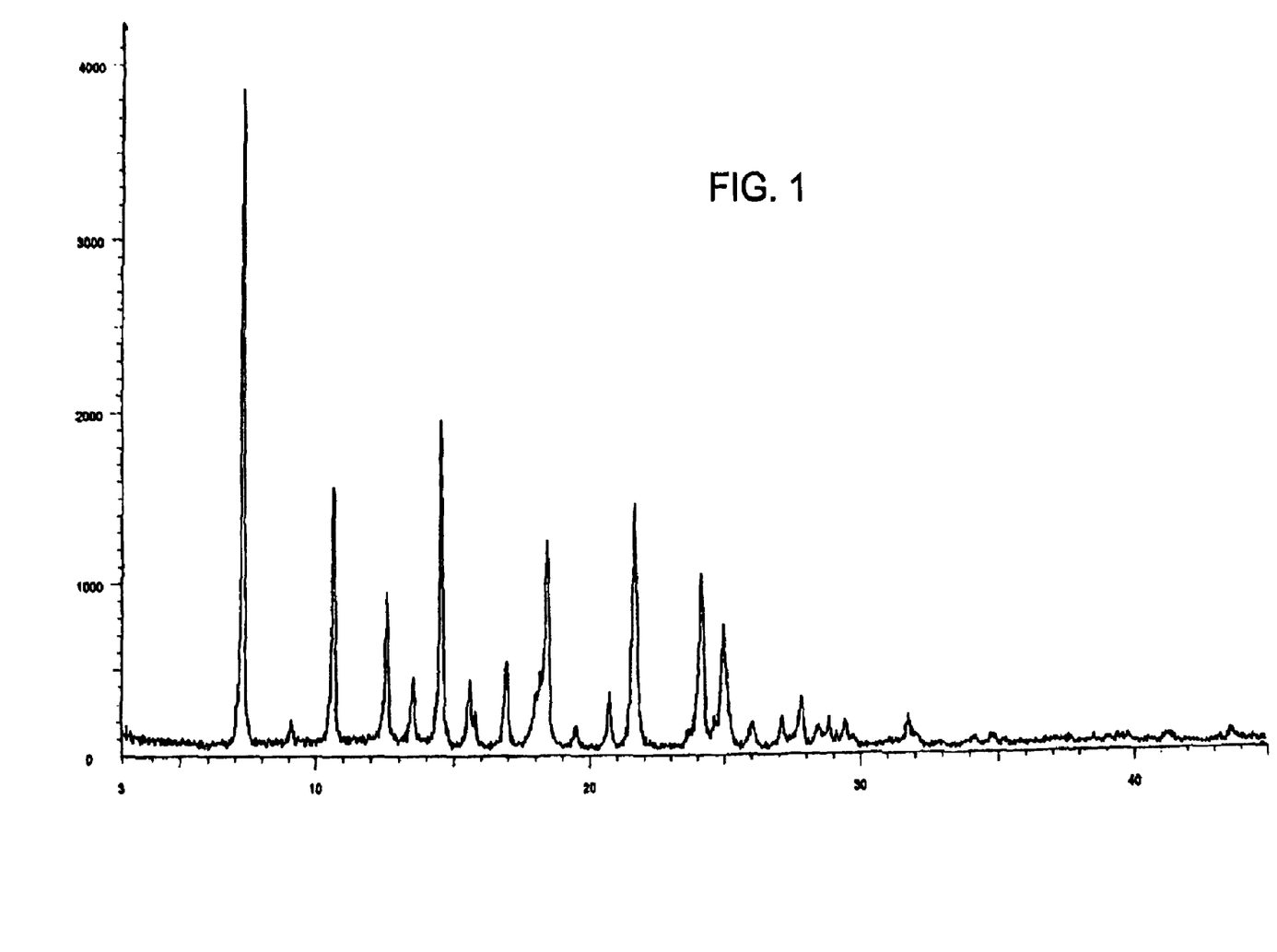
FIG. 1 is an X-ray powder diffraction ("XRPD") pattern for crystalline tadalafil Form A.

Crystalline tadalafil Form A is characterized by its XRPD pattern substantially in accordance with FIG. 1, which pattern comprises significant peaks at about 7.2, 14.5, 10.5, 21.7, and 18.4, ±0.2 degrees 2θ. Form A may be characterized further by the additional XRPD peaks at about 12.5, 16.9, 18.1, 24.1, 24.9, and 27.8, ±0.2 degrees 2θ.

Figure 2:
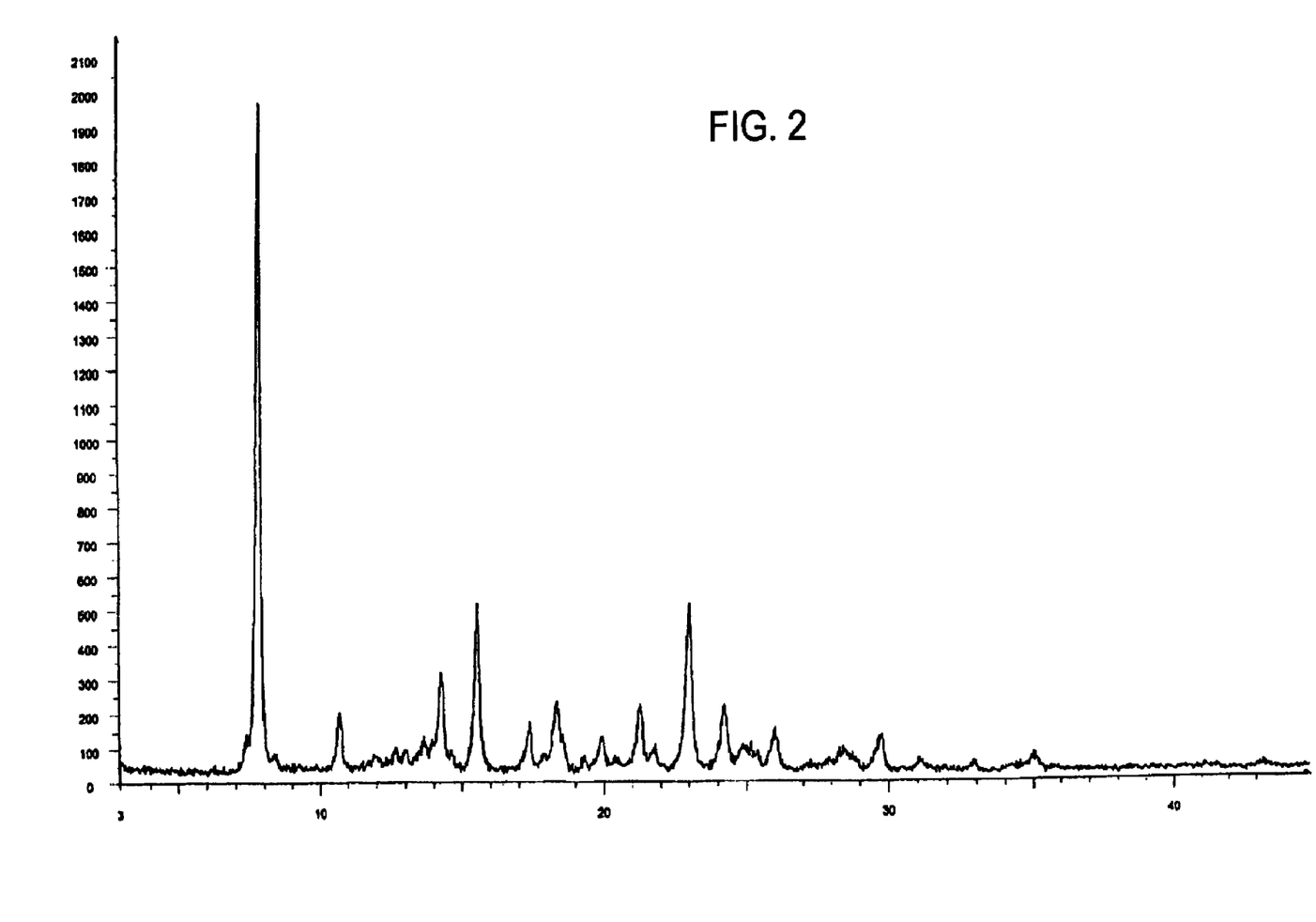
FIG. 2 is an XRPD pattern for crystalline tadalafil Form B.

The crystalline Form B of tadalafil is characterized by its XRPD pattern substantially in accordance with FIG. 2, which pattern comprises significant peaks at about 7.8, 10.6, 14.2, 15.5, 17.3, 18.3, 21.2, 23.0, and 24.2, ±0.2 degrees 2θ.

Figure 3:
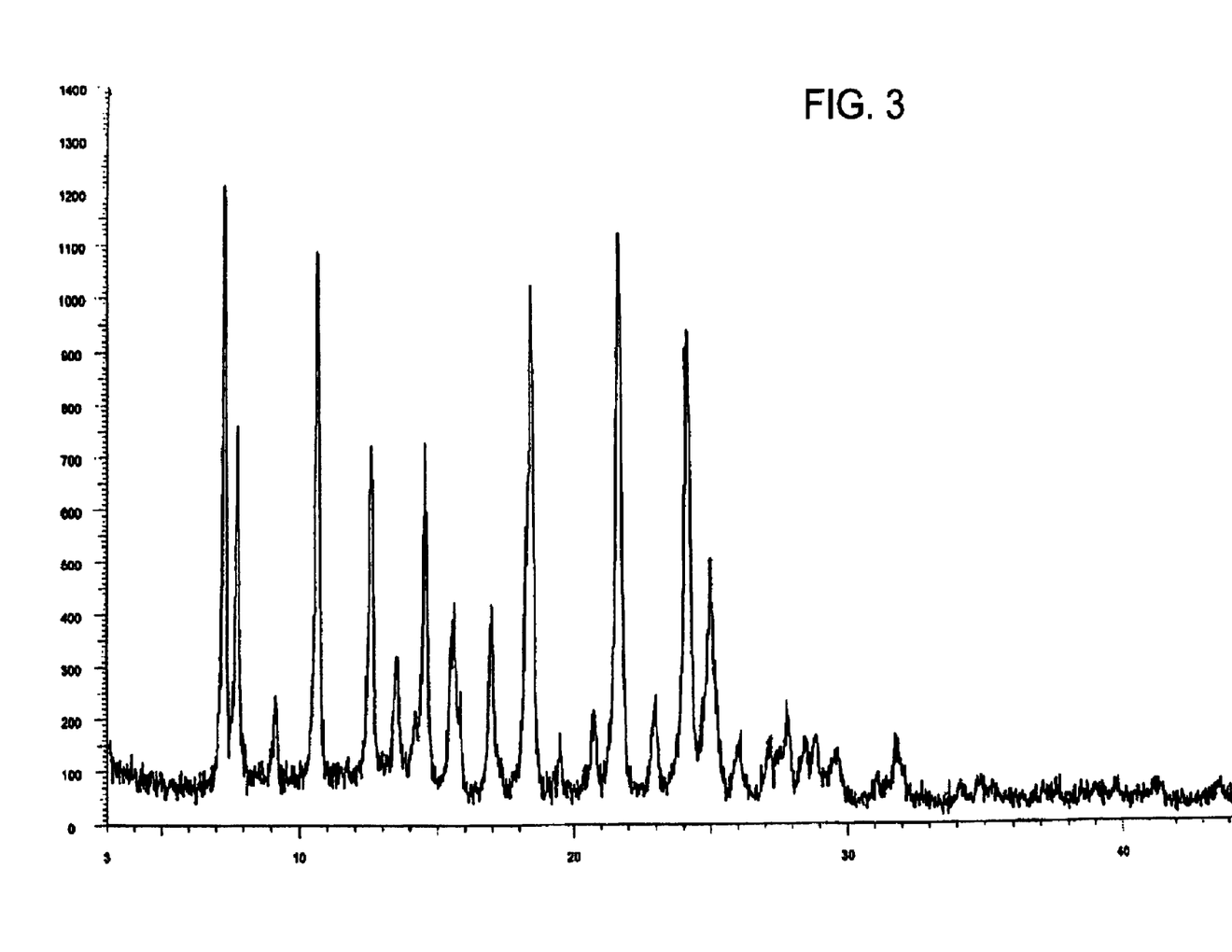
FIG. 3 is an XRPD pattern for a mixture of crystalline tadafil Form A and Form B.

A mixture of crystalline Forms A and B of tadalafil is characterized by its XRPD pattern substantially in accordance with FIG. 3, which pattern comprises significant peaks at about 7.2, 7.7, 10.6, 12.5, 14.1, 14.5, 15.5, 16.9, 18.2, 18.4, 21.7, 24.2, and 25.0, ±0.2 degrees 2θ.

Figure 4:
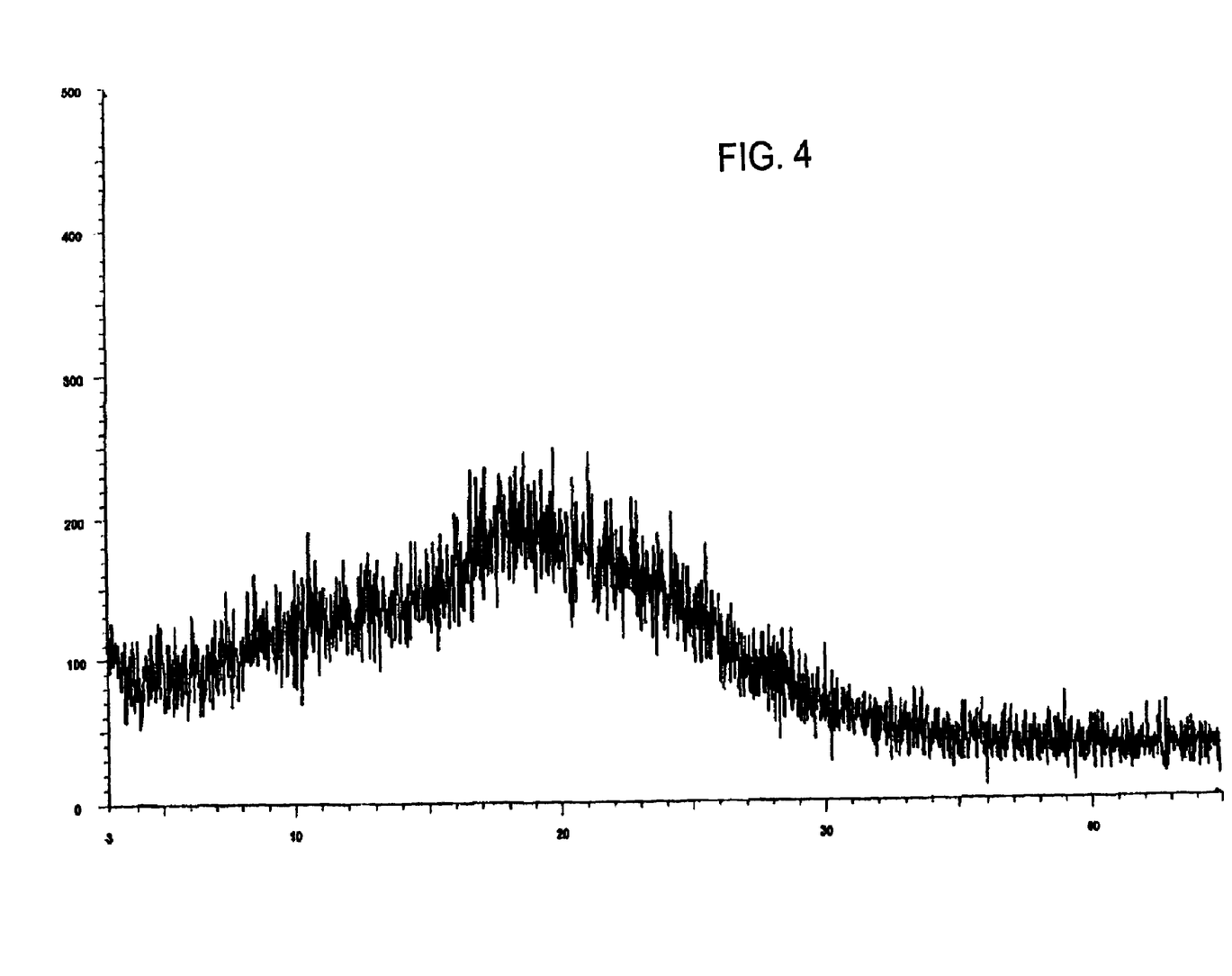
FIG. 4 is an XRPD pattern for amorphous tadalafil.

Amorphous tadalafil has an XRPD pattern showing a halo, which demonstrates the amorphous nature of the substance. The pattern is shown as FIG. 4.

The locations of the XRPD peaks (i.e., the 2θ angles) will be quite constant for a given crystalline substance, subject to small variations due to instrument tolerances. However, the heights of individual peaks can vary considerably between samples of the same substance, frequently because of sample preparation differences. Therefore, when comparing XRPD patterns, the peak locations, and not their relative intensities, will be the better indicator of whether the same substances were present in the samples.

Figure 5A:
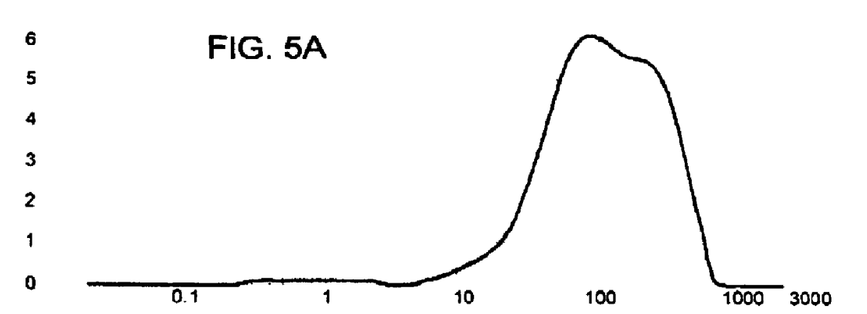
FIGS. 5A, 5B, and 5C are particle size distribution plots for tadalafil prepared according to examples of the invention.
Figure 5B:
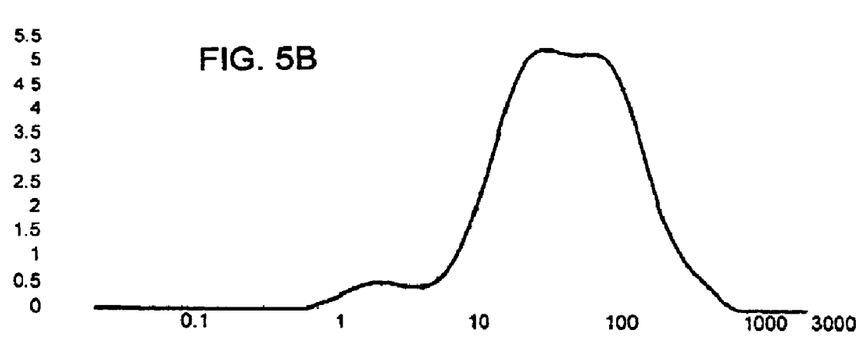
Figure 5C:
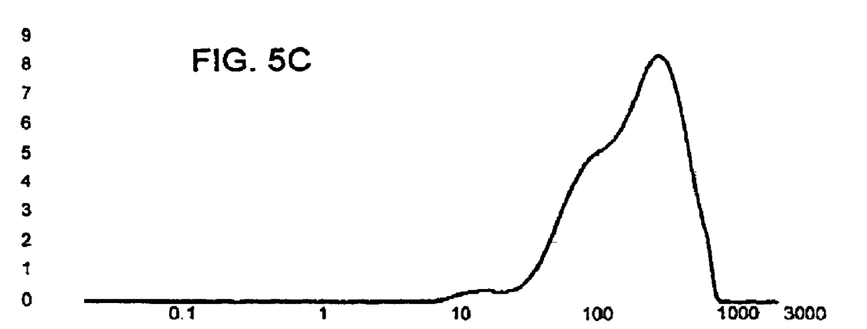
Figure 6:
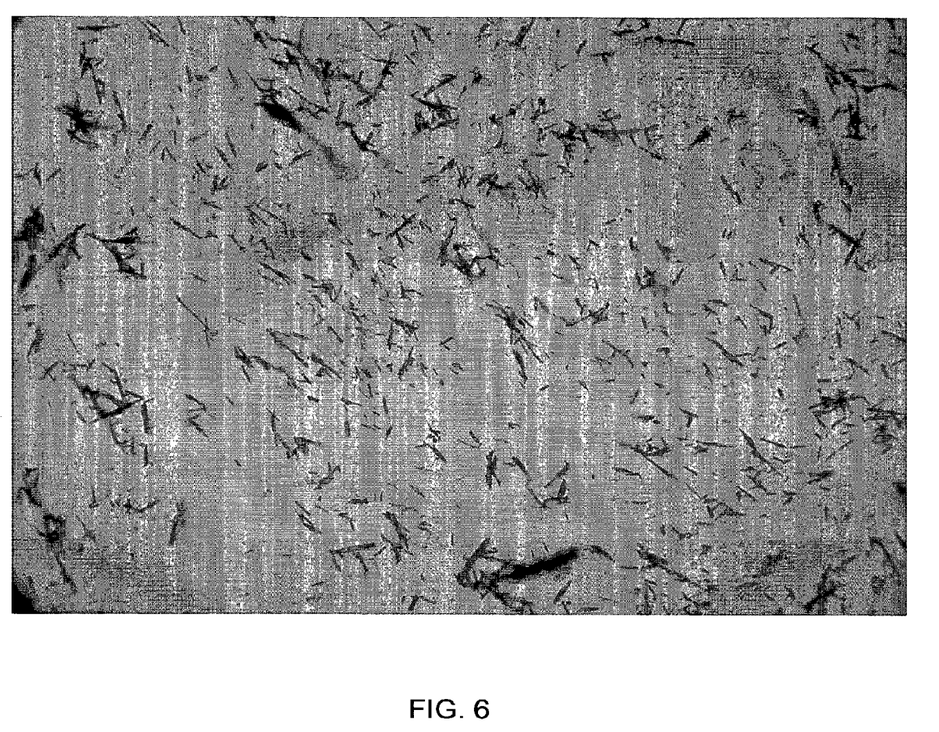
FIG. 6 is a photomicrograph of crystals of tadalafil, prepared according to the invention.

The particle size distribution plots of the drawings were obtained using a MASTERSIZER™ 2000 laser light scattering instrument sold by Malvern Instruments Ltd. of Malvern, Worcestershire, United Kingdom. In the plots, values in the vertical axis represent a volume percentage of particles and the horizontal axis is a logarithmic scale of particle sizes, in μm units.

An aspect of the present invention provides processes for preparing substantially pure crystalline Form A of tadalafil by crystallization, crystallization by adding an anti-solvent to a solution, removal of solvent, or drying a solvate of tadalafil.

In one embodiment, crystalline form A of tadalafil can be prepared by crystallization from a suitable solvent.

A solution is prepared by dissolving tadalafil in a solvent. Useful solvents include, but are not limited to, ketones, $C_3$ to $C_7$ esters, dimethylformamide, dimethylsulphoxide, ethyl alcohol, acetonitrile, chlorinated hydrocarbons such as dichloromethane, t-butanol, ethyl acetate, N,N-dimethylacetamide, dioxane, and mixtures of any two or more thereof. The dissolution procedure optionally can include one or more facilitative measures such as heating, filtering, and diluting the solution.

In another embodiment, crystalline Form A of tadalafil can be prepared by crystallization from solution, by adding an anti-solvent. Examples of useful anti-solvents include $C_5$ to $C_{12}$ hydrocarbons such as heptane or hexane, water, and the like.

The anti-solvent can be added slowly to the solution until a precipitate begins to form. Useful ratios of solvent to the antisolvent range from 1:5 to 1:100, or from 1:2 to 1:20, by volume.

In another embodiment, crystalline Form A, mixtures of Forms A and B, and the amorphous form of tadalafil can be prepared by procedures comprising removal of the solvent from solutions of tadafil.

Removal of solvent can be achieved by distillation, with or without applying a vacuum, evaporation, spray drying, rotational evaporation (such as using a Buchi Rotavapor), agitated thin film drying (ATFD), spin-flash drying, fluid-bed drying, lyophilization or other techniques that will be apparent to those having skill in the art.

Removal of solvent can also be achieved by applying a vacuum to the solution, or by passing a gas, such as air or an inert gas, through the solution.

For mixtures of crystalline form A and form B of tadalafil, the solution can be concentrated to about 50 percent of its original volume. Suitable solvents includes esters such as ethyl acetate, t-butyl acetate, and mixtures thereof.

For amorphous tadalafil, the solution containing tadalafil may be removed or concentrated under vacuum, such as about 530-560 mm Hg.

Suitable solvents include: ketones such as acetone, methyl isobutyl ketone, 2-butanone, 4-methyl pentan-2-one, and methyl ethyl ketone; halogenated hydrocarbons such as dichloromethane, dichloroethane, and carbon tetrachloride; and mixtures thereof.

In one embodiment for preparing amorphous tadalafil, a solution of tadalafil in acetone is subjected to a 530-560 mm Hg vacuum below about 35° C., for about 4-5 hours.

In one embodiment, crystalline Form A of tadalafil is prepared by drying a solvate of tadalafil.

The solvents used for the preparation of solvates of tadalafil include, but are not limited to, acetic acid. The acetic acid solvate of tadalafil can be transformed into crystalline Form A of tadalafil by drying. Drying can be performed by heating the sample under atmospheric or a reduced pressure. Generally, the temperature is from about 40° C. to 95° C. or about 80° C. to 90° C., with or without applying a reduced pressure.

In another embodiment, the present invention provides crystalline Form B of tadalafil.

In an embodiment, crystalline form B of tadalafil can be prepared by crystallization from acetone.

In one embodiment, crystalline Form A of tadalafil can be prepared by crystallization from acetone followed by prolonged cooling of the slurry at 0 to 5° C., such as for about 50 to 60 hours.

The starting material used for the processes of the present invention can be any crystalline or amorphous form of tadalafil, including various solvates and hydrates. The processes of the present invention can also be practiced as the last step of a process that synthesizes tadalafil.

Many processes of the present invention involve crystallization from a particular solvent, i.e., obtaining a solid material from a solution. One skilled in the art will appreciate that the conditions concerning crystallization can be modified without affecting the form of the polymorph obtained. For example, when mixing a solute with a solvent to form a solution, warming of the mixture may be necessary to completely dissolve the starting material. If warming does not form a completely clear solution, the mixture can be diluted or solids separated using techniques such as filtration, centrifugation, decantation, etc. To filter, a hot mixture can be passed through paper, glass fiber or other membrane material, or a bed of a clarifying agent such as celite. Depending upon the equipment used and the concentration and temperature of the solution, the filtration apparatus may need to be preheated to avoid premature crystallization. Those skilled in the art are aware of various alternative methods for solid-liquid separation.

The conditions can also be varied to induce precipitation. A useful way of inducing precipitation is to reduce the solubility of the solute in the solvent. The solubility of the solute can be reduced, for example, by cooling the solution.

In one embodiment, an anti-solvent is added to a solution to decrease its solubility for a particular compound, thus resulting in precipitation.

In all of the above mentioned processes, the crystallization step can be performed with or without stirring. The crystallization step can be performed at about 10° C. to about 120° C. or at reduced temperatures such as about 0° C. to 10° C. The crystallization step can require various times, as can easily be determined through simple experiments.

The process may further include washing the crystalline form.

Drying can be performed under ambient or reduced pressure. For example, drying can be performed under reduced pressure or under atmospheric pressure at a temperature of at about 40° C. to 60° C., or 70° C. to 80° C., or higher, depending on the volatility of the solvent that is being removed. The atmosphere for drying can be air or a partially or completely inert atmosphere, such as by using nitrogen.

The processes of the invention produce tadalafil having particle sizes that are useful for preparing pharmaceutical dosage forms. The particles are characterized by a distribution in which 90 volume percent of the particles have sizes less than about 500 μm. The particles have bulk densities between about 0.15 and about 0.5 g/ml, and bulk densities after tapping between about 0.3 and about 0.7 g/ml.

Tadalafil Form B spontaneously converts to Form A, upon storage at ambient temperatures. Thus, mixtures of Form A and Form B will convert to only Form A.

The processes of the invention prepare tadalafil having high purity. In particular, the content of the trans-tadalafil impurity (6S,12aR)-2,3,6,7,12,12a-hexahydro-2-methyl-6-(3,4-methylened ioxyphenyl)pyrazino[2,1:6,1]pyrido[3,4-b]indole-1,4-dione (having the structure below) in the tadalafil product is less than about 0.1 area-% by HPLC, or less than about 0.05 area-%, or less than about 0.01 area-%.

Further, the content of the chiral tadalafil impurity (6S, 12aS)-2,3,6,7,12,12a-hexahydro-2-methyl-6-(3,4-methylenedioxyphenyl)pyrazino[2,1:6,1]pyrido[3,4-b]indole-1,4-dione (having the structure below) in the tadalafil product of the processes of this invention is less than about 0.1 area-% by HPLC, or less than about 0.05 area-%, or less than about 0.01 area-%.

Certain aspects and embodiments of the invention are further illustrated by the following examples, which should not be construed as limiting the scope of the invention.

EXAMPLE 1

Preparation of Crystalline Form a of Tadalafil by Recrystallization 10 g of tadalafil was placed into a round bottom flask and 25 ml of dimethylformamide was added. The mixture was heated to 60 to 70° C. until a clear solution was obtained. The solution was cooled to 25° C. and maintained under stirring at 25 to 35° C. for about 26 hours. The separated solid was collected by filtration. The solid was washed with 5 ml of dimethylformamide and dried at 80 to 90° C. for 2 to 3 hours to afford 3.7 g of the title compound. Melting point 302° C., moisture content 0.25% w/w. Purity by HPLC: 99.95%. Chiral purity by HPLC: 100%. Trans-tadalafil by HPLC: not detected.

The particle size distribution of the crystals is shown in FIG. 5A. Of the particles, 10 volume percent had diameters less than 31 μm, 50 volume percent had diameters less than 104 μm, and 90 volume percent had diameters less than 321 μm.

This product had a bulk density of 0.344 g/ml, and a tapped bulk density of 0.666 g/ml, determined according to Test Method 616 of *United States Pharmacopeia* 24, United States Pharmacopeial Convention, Inc., Rockville, Md. U.S.A. 1999.

EXAMPLE 2

Preparation of Crystalline Form a of Tadalafil by Recrystallization 1000 ml of acetone were placed into a round bottom flask and 5 g of tadalafil was added. The mixture was stirred at 25 to 35° C. for 30 to 60 minutes. to produce a clear solution. The solution was then cooled to 0 to 5° C. and maintained under stirring at 0 to 5° C. for 48 to 50 hours. The separated solid was collected by filtration. The solid was washed with 5 ml of chilled acetone, then dried by suction for 30 to 60 minutes. The solid was then dried at 60 to 70° C. for 2 to 3 hours to afford 1.2 g of the title compound. Melting point 301-303° C., moisture content 0.07% w/w.

EXAMPLE 3

Preparation of Crystalline Form a of Tadalafil by Recrystallization 20 ml of dimethylsulphoxide was placed into a round bottom flask and 10 g of tadalafil was added. The mixture was stirred at 25 to 35° C. for 30 to 60 minutes, then heated to 60 to 70° C. and stirred at that temperature for 30 to 60 minutes to form a solution. The solution was then cooled to 25 to 35° C. and maintained under stirring at 25 to 35° C. until a solid formed. The solid was isolated by filtration, washed with 5 ml of dimethylsulphoxide then dried under vacuum at 50 to 90° C. for 2 to 3 hours to afford 2.0 g of the title compound. Melting point 298-302° C., moisture content 0.18% w/w.

EXAMPLE 4

Preparation of Crystalline Form a of Tadalafil by Recrystallization 500 ml of ethanol was placed into a round bottom flask and 5 g of tadalafil was added. The mixture was heated to 70 to 80° C. and maintained at 70 to 80° C. for 30 to 60 minutes to form a clear solution. The solution was then cooled to 0 to 5° C. and maintained under stirring at 0 to 5° C. for 30 to 60 minutes. The separated solid was collected by filtration. The solid was washed with 10 ml of chilled (0 to 5° C.) ethanol. The obtained solid was suction dried with vacuum for 30 to 60 minutes, then dried at 60 to 70° C. for 2 to 3 hours to afford 3.0 g of the title compound. Melting point 299-301° C., moisture content 0.32% w/w.

EXAMPLE 5

Preparation of Crystalline Form a of Tadalafil by Anti-Solvent Addition 10 g of tadalafil was placed into a round bottom flask and 20 ml of dimethylsulphoxide was added. The mixture was maintained at 25 to 35° C. for 1 to 1.5 hours to form a clear solution. 400 ml of water was cooled to 0 to 5° C. in another flask, and stirred while the solution of tadalafil in dimethyl-sulphoxide was added slowly at 0 to 5° C. The mixture was maintained at 0 to 5° C. for 2 to 3 hours. The separated solid was filtered, and the solid was washed with 20 ml of chilled water. The solid was suction dried for 30 to 45 minutes, and then dried at 60 to 70° C. for 3 to 4 hours to obtain 9.0 g of the title compound. Melting point 299-300° C., moisture content 0.10% w/w.

EXAMPLE 6

Preparation of Crystalline Form a of Tadalafil by Anti-Solvent Addition 10 g of tadalafil was placed into a round bottom flask and 40 ml of dimethylformamide was added. The mixture was maintained at 25 to 35° C. for 30 to 60 minutes to form a clear solution. The solution was then cooled to 0 to 5° C., poured into 400 ml of chilled water (at 0 to 5° C.), and the mixture was maintained at 0 to 5° C. for 30 to 60 minutes. The separated solid was filtered, washed with 20 ml of chilled water (at 0 to 5° C.), suction dried under vacuum for 30 to 60 minutes, and then dried at 60 to 70° C. for 3 to 4 hours to obtain 8.0 g of the title compound. Melting point 299-302° C., moisture content 0.10% w/w.

EXAMPLE 7

Preparation of Crystalline Form a of Tadalafil by Anti-Solvent Addition 10 g of tadalafil was placed into a round bottom flask and 20 ml of N-methyl pyrrolidone was added. The mixture was maintained at 25 to 35° C. for 30 to 60 minutes to form a clear solution. The solution was then cooled to 0 to 5° C., poured into 400 ml of chilled water, and maintained at 0 to 5° C. for 30 to 60 minutes. The separated solid was filtered, washed with 20 ml of chilled water (at 0 to 5° C.), suction dried under vacuum for 30 to 60 minutes, and then dried at 60 to 70° C. for 3 to 4 hours to obtain 9.0 g of the title compound. Melting point 299-301° C., moisture content 0.28% w/w.

EXAMPLE 8

Preparation of Crystalline Form a of Tadalafil by Anti-Solvent Addition 10 g of tadalafil was placed into a round bottom flask and 550 ml of acetone was added. The mixture was heated to 50 to 60° C. and maintained at 50 to 60° C. for 30 to 60 minutes to form a clear solution. 100 ml of water was added to the reaction mass at 50 to 60° C. The reaction mass was then cooled to 0 to 5° C. and maintained at 0 to 5° C. for 2 to 3 hours. The separated solid was filtered, washed with 10 ml of chilled water (at 0 to 5° C.), suction dried under vacuum for 30 to 60 minutes, and then dried at 60 to 70° C. for 3 to 4 hours to obtain 3.2 g of the title compound. Melting point 298-299° C., moisture content 0.56% w/w.

EXAMPLE 9

Preparation of Crystalline Form a of Tadalafil by Anti-Solvent Addition 5 g of tadalafil was placed into a round bottom flask and 250 ml of acetonitrile was added at 25 to 35° C. The mixture was heated to 80 to 85° C. and maintained at the same temperature for 30 to 60 minutes to form a clear solution. The solution was poured into 500 ml of chilled water (at 0 to 5° C.) and the mixture was maintained at 0 to 5° C. for 30 to 60 minutes. The separated solid was filtered, the solid was washed with 10 ml of chilled water, suction dried under vacuum for 30 to 60 minutes, and then dried at 60 to 70° C. for 3 to 4 hours to obtain 4.6 g of the title compound. Melting point 299-301° C.

EXAMPLE 10

Preparation of Crystalline Form a of Tadalafil by Anti-Solvent Addition 10 g of tadalafil was placed into a round bottom flask and 800 ml of acetonitrile was added at 25 to 35° C. The mixture was stirred at 25 to 35° C. for 30 to 60 minutes, then was heated to 80 to 85° C. and maintained for 30 to 60 minutes to form a clear solution. 800 ml of water was added slowly to the solution. The mixture was gradually cooled to 25 to 35° C. and maintained for 2 to 3 hours. The separated solid was filtered, washed with 20 ml of a 1:1 mixture of acetonitrile and water, suction dried under vacuum for 30 to 60 minutes, and then dried at 80 to 90° C. for 3 to 4 hours to obtain 4.5 g of the title compound. Melting point 298-299.5° C., moisture content 0.23% w/w.

EXAMPLE 11

Preparation of Crystalline Form a of Tadalafil by Recrystallization Through Concentration 300 ml of acetone was placed into a round bottom flask and 5 g of tadalafil was added at 25 to 35° C. The mixture was heated to 50 to 60° C. and maintained for 30 to 60 minutes, then transferred into a Buchi Rotavapor flask and cooled to 25 to 35° C. The solvent was distilled completely under vacuum at a pressure of 350-400 mm Hg at 25 to 35° C. After completion of the distillation, the material was scraped from the Rotavapor flask and dried at 50 to 60° C. for 3 to 4 hours to obtain 4.5 g of the title compound. Melting point 299-301° C., moisture content 0.20% w/w.

The particle size distribution of the crystals is shown in FIG. 5B. Of the particles, 10 volume percent had diameters less than 9.9 μm, 50 volume percent had diameters less than 40 μm, and 90 volume percent had diameters less than 148 μm.

This product had a bulk density of 0.181 g/ml, and a tapped bulk density of 0.434 g/ml, determined according to Test Method 616 of *United States Pharmacopeia* 24, United States Pharmacopeial Convention, Inc., Rockville, Md. U.S.A. 1999.

EXAMPLE 12

Preparation of Crystalline Form a of Tadalafil by Recrystallization Through Concentration 600 ml of acetone was placed into a round bottom flask and 10 g of tadalafil was added at 25 to 35° C. The mixture was heated to 50 to 60° C. and maintained for 30 to 60 minutes to form a clear solution. 100 ml of water was added to the solution at 50 to 60° C. 75 percent of the solvent volume was distilled from the reaction mass under vacuum, at 50 to 60° C. After completion of the distillation, the solution was cooled to 0 to 5° C. and maintained at 0 to 5° C. for 30 to 60 minutes.

The separated solid was filtered, washed with 10 ml of chilled water, suction dried under vacuum for 30 to 60 minutes, and then dried at 60 to 70° C. for 3 to 4 hours to obtain 8.6 g of the title compound. Melting point 300-302° C., moisture content 0.22% w/w.

EXAMPLE 13

Preparation of Crystalline Form a of Tadalafil by Recrystallization Through Concentration 550 ml of acetone was placed into a round bottom flask and 10 g of tadalafil was added at 25 to 35° C. The mixture was heated to 50 to 60° C. and maintained for 30 to 60 minutes to form a clear solution. 100 ml of water was added to the solution at 50 to 60° C., and the mixture was maintained under the same conditions for 30-60 minutes. 75 percent of the solvent volume was distilled from the reaction mass at 50 to 60° C. After completion of the distillation, the reaction mass was cooled to 0 to 5° C. and maintained at 0 to 5° C. for 30 to 60 minutes. The separated solid was filtered, washed with 10 ml of chilled water, suction dried under vacuum for 30 to 60 minutes, and then dried at 60 to 70° C. for 3 to 4 hours to obtain 8.5 g of the title compound. Melting point 299-301° C., moisture content 0.22% w/w.

EXAMPLE 14

Preparation of Crystalline Form a of Tadalafil by Recrystallization Through Concentration 275 ml of acetone was placed into a round bottom flask and 5 g of tadalafil was added at 25 to 35° C. The reaction mass was heated to 50 to 60° C. and maintained for 30 to 60 minutes to form a clear solution. 25 percent of the solvent volume was distilled from the solution at atmospheric pressure, at 50 to 60° C. After completion of the distillation, the reaction mass was cooled to 0 to 5° C. and maintained at 0 to 5° C. for 30 to 70 minutes. The separated solid was filtered, washed with 2.5 ml of chilled acetone (at 0 to 5° C.), suction dried under vacuum for 30 to 60 minutes, and then dried at 60 to 70° C. for 3 to 4 hours to obtain 4.6 g of the title compound. Melting point 299-301° C., moisture content 0.12% w/w.

EXAMPLE 15

Preparation of Crystalline Form a of Tadalafil by Recrystallization Through Concentration 275 ml of acetone was placed into a round bottom flask and 5 g of tadalafil was added at 25 to 35° C. The reaction mass was heated to 50 to 60° C. and maintained for 30 to 60 minutes to form a clear solution. 50 percent of the solvent volume was distilled from the reaction mass at atmospheric pressure, at 50 to 60° C. After completion of the distillation, the reaction mass was cooled to 20 to 25° C. and maintained at 20 to 25° C. for 30 to 60 minutes. The separated solid was filtered, washed with 2.5 ml of acetone (at 20 to 25° C.), and dried at 60 to 70° C. for 3 to 4 hours to obtain 3.2 g of the title compound. Melting point 299-301° C., moisture content 0.17% w/w.

The particle size distribution of the crystals is shown in FIG. 5C. Of the particles, 10 volume percent had diameters less than 58 µm, 50 volume percent had diameters less than 193 µm, and 90 volume percent had diameters less than 428 µm.

This product had a bulk density of 0.435 g/ml, and a tapped bulk density of 0.626 g/ml, determined according to Test Method 616 of United States Pharmacopeia 24, United States Pharmacopeial Convention, Inc., Rockville, Md. U.S.A. 1999.

EXAMPLE 16

Preparation of Crystalline Form a of Tadalafil by Drying a Tadalafil Solvate 130 ml of glacial acetic acid was placed into a round bottom flask and 10 g of tadalafil was added. The mixture was heated to 70 to 80° C. and maintained for 30 to 60 minutes to form a clear solution, and then was cooled to 25 to 35° C. and maintained at 25 to 35° C. for 30 to 60 minutes. The separated solid was filtered, washed with 10 ml of methyl t-butyl ketone, suction dried for 30 to 60 minutes, and dried at 60 to 70° C. for 2 to 3 hours. The solid was further dried at 80 to 90° C. under vacuum to afford 8.3 g of the title compound. Melting point 299-301° C.

EXAMPLE 17

Preparation of Crystalline Form B of Tadalafil 10 g of tadalafil was placed into a round bottom flask and 700 ml of acetone was added. The mixture was heated to 50 to 60° C. and maintained for 30 to 45 minutes, then cooled to 25 to 35° C. and maintained for 2 to 3 hours. The separated solid was filtered, washed with 10 ml of acetone, and dried at 60 to 70° C. for 3 to 4 hours to afford 6 g of the title compound, having the XRPD pattern of FIG. 2. Moisture content 0.06% w/w. Purity by HPLC: 99.92%. Chiral purity by HPLC: 100%. Trans-tadalafil by HPLC: not detected.

EXAMPLE 18

Preparation of a Mixture of Form A and Form B of Tadalafil 10 g of tadalafil was dissolved in 800 ml of ethyl acetate and heated to 60 to 70° C., then maintained at 70 to 80° C. for 30 to 60 minutes to produce a clear solution. 50 percent of the solvent volume was distilled from the solution under vacuum, then the solution was cooled to 25 to 35° C. and maintained for 2 to 3 hours. The separated solid was filtered, washed with 10 ml of ethyl acetate, and dried under reduced pressure at a temperature of 80 to 90° C. to yield 5 g of the title mixture, having the XRPD pattern of FIG. 3. Moisture content 0.15% w/w. Purity by HPLC: 99.9%. Trans-tadalafil by HPLC: not detected.

EXAMPLE 19

Preparation of Amorphous Tadalafil 10 g of tadalafil was placed into a round bottom flask and 550 ml of acetone was added. The mixture was heated to 60 to 65° C. and maintained for 30 to 60 minutes to obtain a clear solution. The solution was then cooled to 25 to 35° C. and subjected to a vacuum of 550 mm Hg in a Rotavapor flask at temperatures between 25 and 40° C. for 4 to 5 hours. The resultant solid was dried at 80 to 90° C. under vacuum to afford 6.1 g of the title compound, having the XRPD pattern of FIG. 4. Moisture content 0.15% w/w. Purity by HPLC: 99.98%.

EXAMPLE 20

25 g of tadalafil was dissolved in 1375 ml of acetone, by heating to 50 to 66° C. and stirring for 30 to 45 minutes. The solution was cooled to 25 to 35° C. and maintained for 2 to 3 hours, as crystals formed. The crystals were removed by filtration, washed with 12.5 ml of acetone, and dried at 60 to 70° C. for 3 to 4 hours to give 6 g of tadafil Form B crystals, as shown by the XRPD pattern in accordance with FIG. 2.

The Form B crystals were sealed in a polyethylene bag and stored under ambient conditions for 40 hours, after which the XPRD pattern was in accordance with FIG. 1, indicating conversion of the tadalafil Form B into Form A.

EXAMPLE 21

25 g of tadalafil was dissolved in 2000 ml of ethyl acetate by heating to 60 to 70° C., then to 70 to 80° C. and stirred for 30 to 60 minutes. Half of the solvent volume was removed by distillation under vacuum, and the solution was cooled to 25 to 35° C. and maintained for 2 to 3 hours as crystals formed. The crystals were removed by filtration, washed with 25 ml of ethyl acetate, and dried under vacuum at 80-90° C. to yield 5 g of a mixture of tadalafil Form A and Form B, having an XRPD similar to that of FIG. 3.

A sample was stored in a sealed polyethylene bag under ambient conditions for 3 to 4 days, and then was found to have an XRPD pattern in accordance with FIG. 1, indicating conversion of the tadalafil Form B into Form A.

COMPARATIVE EXAMPLE

Cis-2,3,6,7,12,12a-hexahydro-6-(4-ethylphenyl)-2-cyclopropylmethyl-pyrazino[2',1':6,1]pyrido[3,4-b]indole-1,4-dione, prepared according to Example 73 of U.S. Pat. No. 5,859,006, was reacted with methylamine as described in Example 95 of the patent. 18.4 g of the solid obtained after evaporating the solvent was dissolved in 5720 ml of isopropanol at 75° C., and was then cooled to 10° C. over about 90 minutes, with stirring. Formed crystals were isolated by filtration, washed with 16 ml of isopropanol, and dried at 55° C., yielding 10.5 g of tadalafil. A sample of the dried material was used to obtain an XRPD pattern, having the strongest peaks (in the order of higher to lower intensities) at 7.25, 14.5, 18.4, 25.0, 12.5, 21.7, 24.7, 10.6, and 24.2 degrees 2θ. Based on its X-ray diffraction pattern, the prepared material appears to correspond with Form A of tadalafil. Chiral purity by HPLC: 99.46%, chiral tadalafil impurity 0.54%. Trans-tadalafil impurity by HPLC: 0.43%.

What is claimed is:

1. A process for preparing crystalline Form A of tadalafil, comprising crystallization from a solution of tadalafil in a solvent comprising a $C_3$-$C_7$ ester, a ketone, dimethylformamide, N,N-dimethylacetamide dioxane, N-methyl pyrrolidone, or a mixture of any two or more thereof.

2. The process of claim 1, wherein crystallization results from cooling a solution of tadalafil.

3. The process of claim 1, wherein crystallization results from concentrating a solution of tadalafil.

4. The process of claim 1, wherein crystallization results from combining an anti-solvent with a solution of tadalafil.

5. The process of claim 1, wherein crystallization results from combining a $C_5$ to $C_{12}$ hydrocarbon or water with a solution of tadalafil.

6. The process of claim 1, wherein a solvent comprises acetone, methyl isobutyl ketone, 2-butanone, 4-methylpentan-2-one, methyl ethyl ketone, or a mixture of any two or more thereof.

7. The process of claim 1, wherein a solvent comprises acetone.

8. The process of claim 1, wherein a solvent comprises acetone and crystallization results from combining an anti-solvent with a solution of tadalafil.

9. The process of claim 1, wherein a solvent comprises acetone and crystallization results from combining water with a solution of tadalafil.

* * * * *